(12) United States Patent
Cline et al.

(10) Patent No.: US 8,054,184 B2
(45) Date of Patent: Nov. 8, 2011

(54) IDENTIFICATION OF SURGICAL INSTRUMENT ATTACHED TO SURGICAL ROBOT

(75) Inventors: Edward Arthur Cline, Campbell, CA (US); Alan Eton Loh, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 552 days.

(21) Appl. No.: 12/183,987

(22) Filed: Jul. 31, 2008

(65) Prior Publication Data
US 2010/0026456 A1 Feb. 4, 2010

(51) Int. Cl.
*G08B 13/14* (2006.01)
(52) U.S. Cl. ............ 340/572.1; 340/10.1; 340/572.7; 600/101; 600/104; 901/46; 901/9
(58) Field of Classification Search ........... 340/572.7, 340/10.1, 572.1; 600/101, 103, 104, 109, 600/112; 901/46, 9; 343/7; 367/96
See application file for complete search history.

(56) References Cited

U.S. PATENT DOCUMENTS

| | | | | |
|---|---|---|---|---|
| 4,805,232 A | * | 2/1989 | Ma | 455/291 |
| 5,305,002 A | * | 4/1994 | Holodak et al. | 340/572.7 |
| 5,373,303 A | * | 12/1994 | D'Hont | 343/788 |
| 5,378,880 A | * | 1/1995 | Eberhardt | 235/439 |
| 5,694,139 A | * | 12/1997 | Saito et al. | 343/866 |
| 6,229,420 B1 | * | 5/2001 | Bauml et al. | 335/205 |
| 7,268,688 B2 | * | 9/2007 | Juds | 340/572.8 |
| 7,515,049 B2 | * | 4/2009 | Sharma et al. | 340/572.6 |
| 2003/0112127 A1 | * | 6/2003 | Reuker | 340/10.42 |
| 2006/0142656 A1 | * | 6/2006 | Malackowski et al. | 600/424 |
| 2007/0208251 A1 | * | 9/2007 | Anderson et al. | 600/424 |
| 2009/0167498 A1 | * | 7/2009 | Fukuda et al. | 340/10.1 |

FOREIGN PATENT DOCUMENTS
EP 1944878 A1 * 7/2008

OTHER PUBLICATIONS

Vertut, Jean et al., *Robot Technology: Teleoperation and Robotics Evolution and Development*, 1986, vol. 3A, 332 pages, English translation Prentice-Hall, Inc., Inglewood Cliffs, NJ, USA.

\* cited by examiner

*Primary Examiner* — Eric M Blount

(57) ABSTRACT

A radio frequency identification (RFID) tag is embedded on a surgical instrument and a radio frequency identification (RFID) reader is provided on a surgical robot to allow identification of the attached surgical instrument. The RFID tag includes an RFID circuit assembly, a first pot core half, and a first toroidal wire coil that fits within the first pot core half and is electrically coupled to the RFID circuit assembly to modulate received radio frequency (RF) energy. The RFID reader includes an RFID transceiver circuit, a second pot core half, and a second toroidal wire coil that fits within the second pot core half and is electrically coupled to the transceiver circuit to transmit RF energy and receive modulated RF energy from the first wire coil only when the first pot core half is substantially aligned with and proximate to the second pot core half.

13 Claims, 4 Drawing Sheets

IDENTIFICATION OF SURGICAL INSTRUMENT ATTACHED TO SURGICAL ROBOT

BACKGROUND

1. Field

Embodiments of the invention relate to the field of radio frequency identification (RFID), and more specifically, to radio frequency identification of RFID tags that are located close to an RFID receiver while rejecting RFID tags that are slightly further away.

2. Background

Robotic surgical systems allow surgeons to perform minimally invasive surgery using endoscopic instruments that are controlled by robotic manipulators. Such systems may allow a more intuitive use of the instruments by translating camera views and surgeon hand movements to correspond to what the surgeon would expect in an open surgery.

Typically a robotic surgical system provides a small number of robotic manipulators, perhaps three or four, to which a variety of surgical instruments may be attached. The surgical instruments may be changed during the course of a surgery. The robotic manipulators are typically wrapped with a sterile drape that provides a sterile barrier between the robotic manipulators and the attached surgical instruments.

The robotic surgical system may need to know the identity of the attached instruments so the system can provide the appropriate translation of the camera views and surgeon hand movements. The system may provide information about the identity of the attached instruments to the surgeon to maintain awareness of the current configuration of the system. In some cases, the instruments may be capable of attachment in more than one orientation. The robotic surgical system may need to know the orientation of the attached instruments so the system can provide the appropriate translation of the camera views and surgeon hand movements.

It would be desirable to provide identification of a surgical instrument attached to a surgical robot and separated by a sterile barrier. It would also be desirable to provide the orientation of the surgical instrument.

SUMMARY

A radio frequency identification (RFID) tag is embedded on a surgical instrument and a radio frequency identification (RFID) reader is provided on a surgical robot to allow identification of the attached surgical instrument. The RFID tag includes an RFID circuit assembly, a first pot core half, and a first toroidal wire coil that fits within the first pot core half and is electrically coupled to the RFID circuit assembly to modulate received radio frequency (RF) energy. The RFID reader includes an RFID transceiver circuit, a second pot core half, and a second toroidal wire coil that fits within the second pot core half and is electrically coupled to the transceiver circuit to transmit RF energy and receive modulated RF energy from the first wire coil only when the first pot core half is substantially aligned with and proximate to the second pot core half.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known devices, structures and techniques have not been shown in detail in order not to obscure the understanding of this description.

Figure 1:
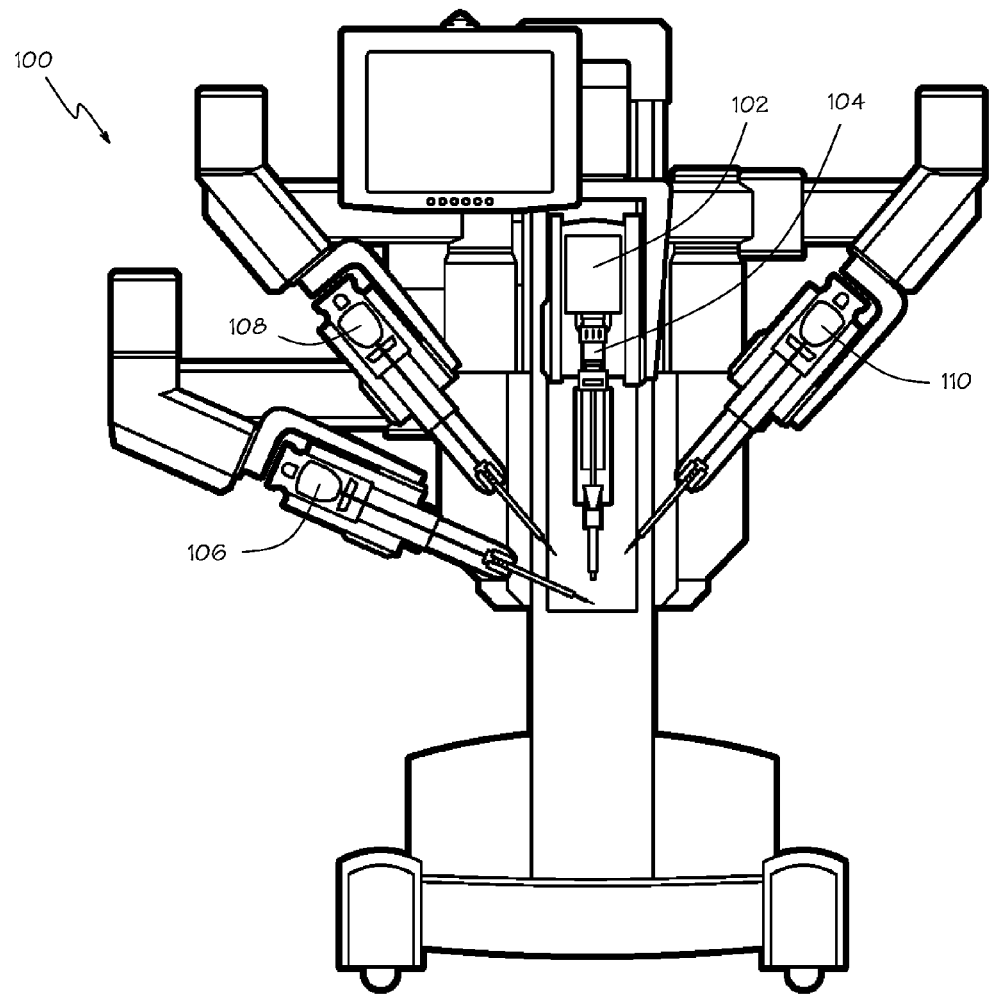
FIG. 1 shows a pictorial view of a patient side cart that includes an embodiment of the invention.

FIG. 1 shows a pictorial view of a patient side cart 100 that supports robotic surgical instruments 104, 106, 108, 110 for performing robotically assisted surgeries. The present invention will be described in the context of its application to an endoscopic camera system 102, 104. It will be appreciated that the invention is not limited to use on an endoscopic camera. For example, the present invention may be applied to any of the robotic surgical instruments.

The robotic surgical instruments 102, 104, 106, 108, 110 are detachably coupled to surgical robots on the patient side cart 100. The surgical robots may provide motive forces to the surgical instruments to position them and to operate end effectors on the instruments. The surgical robots may receive information from the instruments such as the amount of force being applied by the instrument. In particular, the patient side cart 100 may support an endoscopic camera system 102, 104.

Figure 2:
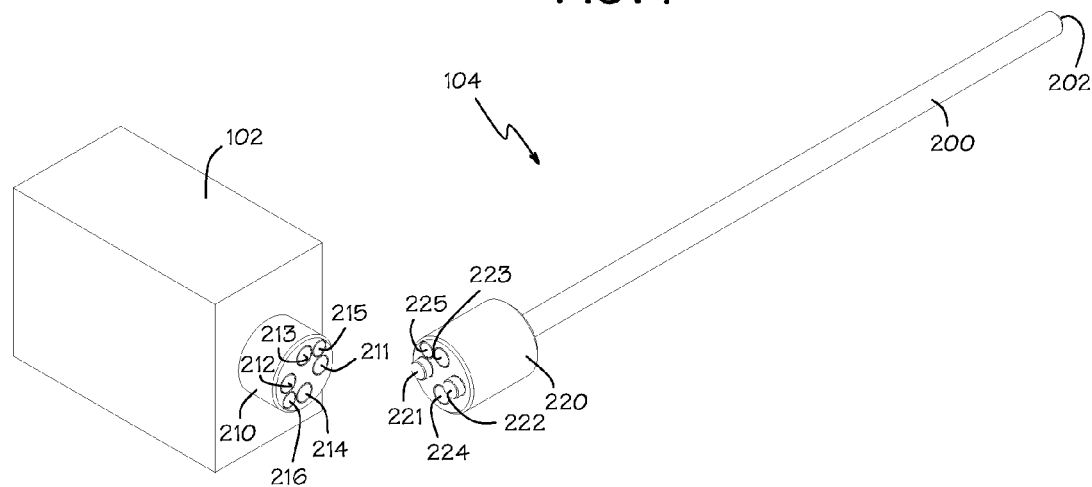
FIG. 2 shows a pictorial view of an endoscope and an endoscopic camera in a separated configuration.

FIG. 2 shows a pictorial view of the endoscopic camera 102 and the endoscope 104 in a separated configuration so the interface between them can be seen. Generally the patient side cart 100, including the endoscopic camera 102, will be draped with a sterile barrier. The robotic surgical instruments 104, 106, 108, 110 will be sterilized. Therefore it is necessary to couple the sterile instruments to the patient side cart 100 with the sterile barrier separating them. The sterile barrier may include specially formed portions to facilitate the coupling of the instruments to the surgical robots.

The endoscopic camera system includes a camera 102 and an endoscope 104. The camera may be located on the non-sterile side of the sterile barrier. The camera may include image sensors, focusing optics, and light sources. The endoscope 104 may be coupled to a mating portion 210 of the camera 102 with the sterile barrier separating them. The camera 102 may provide two image ports 213, 214 that are coupled to the image sensors to form stereoscopic images. The camera 102 may provide illumination from the light sources at the two light ports 211, 212.

The endoscope 104 includes a shaft 200 that can be inserted through an incision to place a distal end 202 of the endoscope 104 adjacent a surgical site. The endoscope 104 may provide a passive extension of the camera 102 into the surgical site.

Lenses at the distal end 202 of the endoscope 104 may relay surgical images to camera ports 223, 224 that are coupled to the image ports 213, 214 on the camera 102. Light from the light ports 211, 212 on the camera 102 may be coupled to light receivers 221, 222 on the endoscope 104. Light pipes may convey the light from the light receivers 221, 222 to the distal end 202 of the endoscope to illuminate the surgical site.

A radio frequency identification (RFID) tag 225 is embedded on the proximal end 220 of the surgical instrument 104. A radio frequency identification (RFID) reader is provided within the endoscopic camera 102 to allow identification of the attached endoscope 104 from its RFID tag 225. The RFID tag 225 and an antenna 215 of the RFID reader are of a unique construction to allow the antenna and/or tag to be embedded in a metal structure that may be used to form the mating portion 210 of the camera 102 and/or the proximal end 220 of the endoscope 104. The structure of the RFID tag 225 and antenna 215 permit reliable operation in what may be an electrically noisy environment. For example, there may be electrical interference created by high voltage discharges from electrocautery devices in close proximity to the RFID tag 225.

Figure 3:
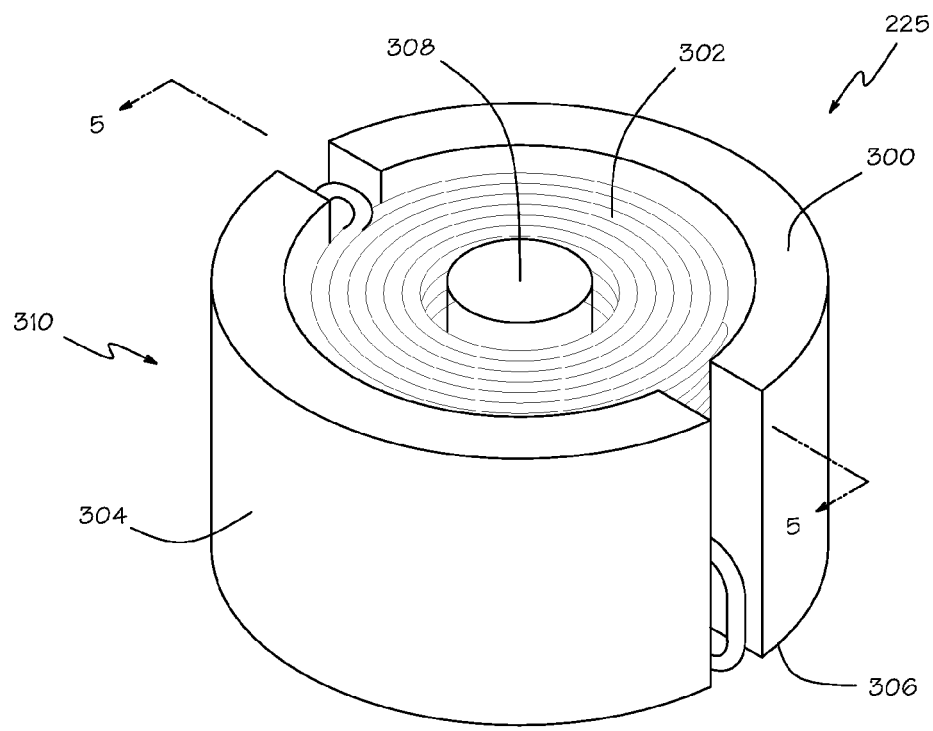
FIG. 3 is a pictorial view of an RFID tag that embodies the invention.
Figure 4:
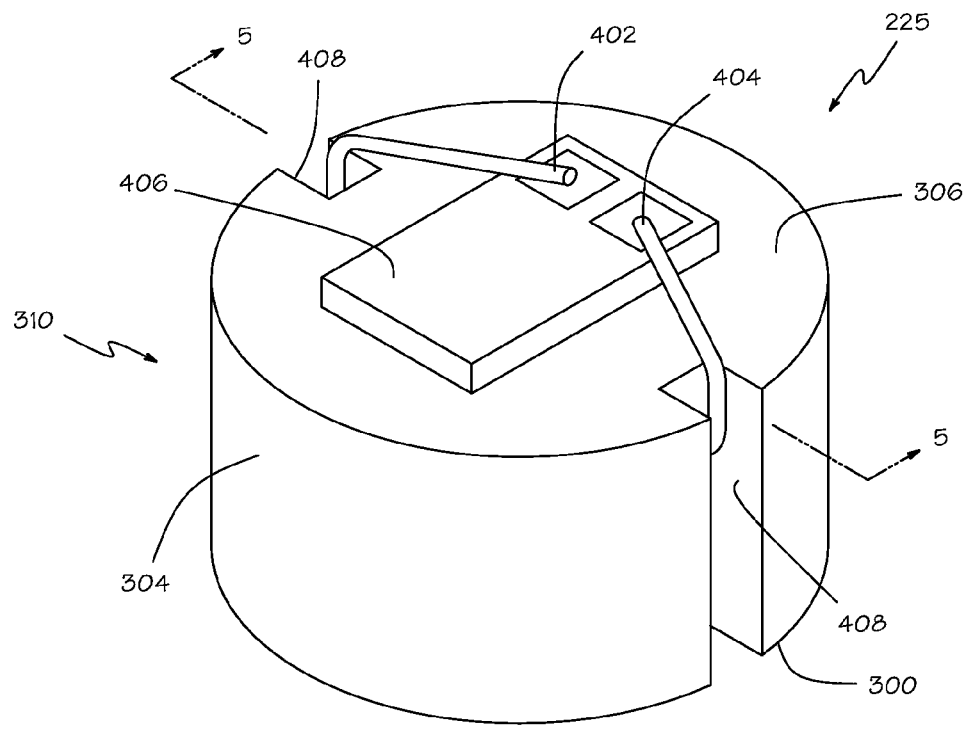
FIG. 4 is a pictorial view of the opposite side of the RFID tag shown in FIG. 3.
Figure 5:
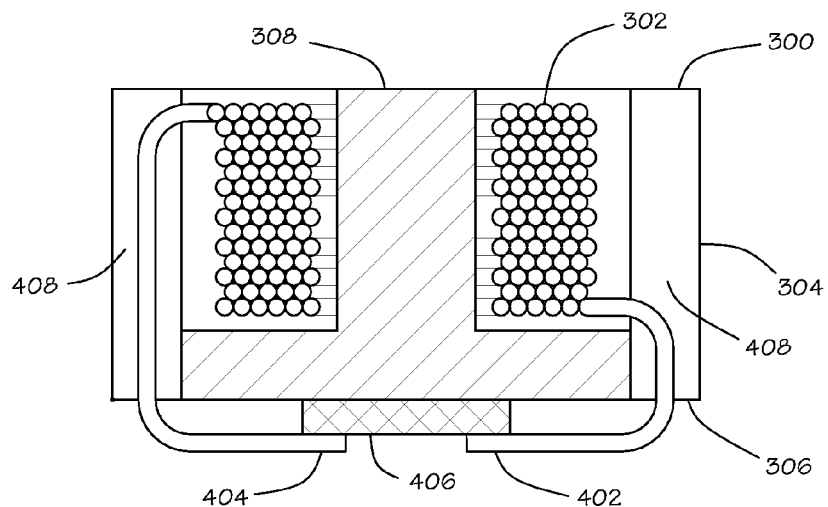
FIG. 5 is a cross-section of the RFID tag along line 5-5 of FIGS. 3 and 4.

FIGS. 3 and 4 are pictorial views of the RFID tag 225. FIG. 5 is a cross-section of the RFID tag 225 along line 5-5 of FIGS. 3 and 4. FIG. 3 shows the surface 300 of the RFID tag 225 that faces the RFID antenna 215. FIG. 4 shows the opposite surface 306 of the RFID tag 225.

The RFID tag 225 of the present invention includes a toroidal wire coil 302 that fits within half of a pot core 310. The pot core half 310 has a cylindrical base 306 with a cylindrical center pole 308 and a cylindrical outer pole 304 extending from a first side of the base. The pot core half 310 may be constructed of ferrite or other material with a high magnetic permeability that does not maintain a significant magnetic field when an external field is removed. The toroidal wire coil 302 fits within the outer pole 304 of the pot core and around the center pole 308. The toroidal wire coil 302 may be potted in the pot core half 310.

The two ends 402, 404 of the toroidal wire coil 302 are electrically coupled to an RFID circuit assembly 406 to modulate received radio frequency (RF) energy. The RFID circuit assembly 406 is powered by the received RF energy. The RFID circuit assembly 406 is configured to encode identification information in the transmitted RF energy by load modulation which may allow the surgical robot to identify the surgical instrument and confirm that it is attached. The two ends 402, 404 of the toroidal wire coil 302 may extend through one or more gaps 408 in an outer pole of the pot core half 310 as shown in FIGS. 4 and 5. The RFID circuit assembly 406 may be bonded to the opposite surface 306 of the RFID tag 225. The RFID circuit assembly 406 may be encapsulated on the pot core half 310.

Figure 6:
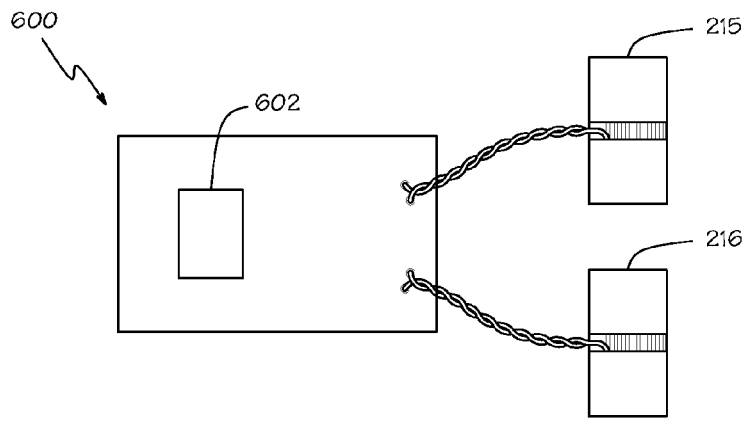
FIG. 6 is a plan view of an RFID reader that embodies the invention.

FIG. 6 shows a plan view of an RFID reader 600 that may be included in the endoscopic camera 102. The RFID reader 600 includes an RFID transceiver circuit 602, and one or more RFID antennas 215, 216. Each RFID antenna 215, 216 is substantially similar in construction to the previously described RFID tag 225. The RFID reader 600 may transmit and receive radio frequency (RF) energy having a relatively low frequency. For example, the frequency may be substantially 125 kHz. The RFID circuit assembly 406 in the RFID tag 225 may include a tuning capacitor to provide an LC resonant frequency that corresponds to the frequency of the RFID reader 600, e.g. substantially 125 kHz.

Figure 7:
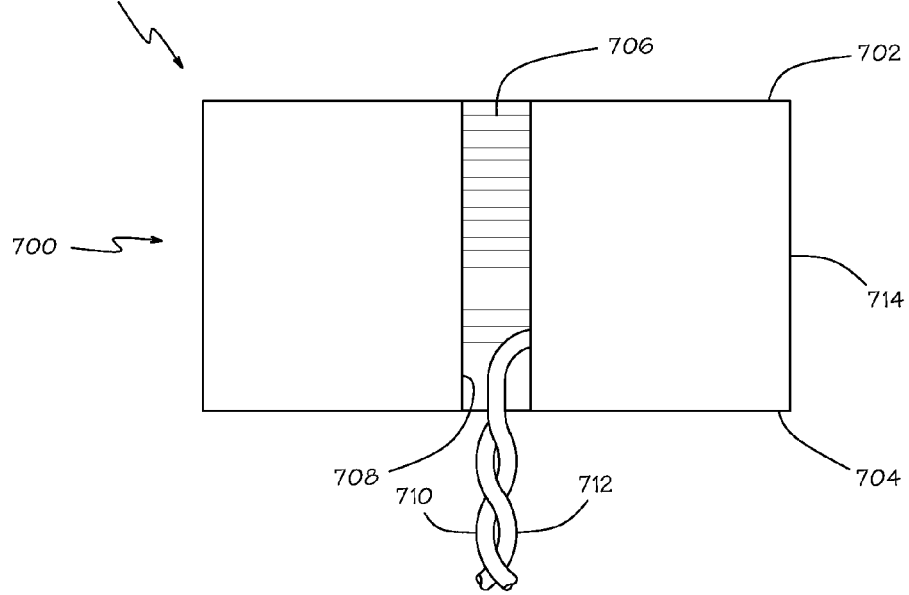
FIG. 7 is a side elevation of an RFID antenna that embodies the invention.

FIG. 7 shows a side elevation of one of the RFID antennas 215 of the present invention. The RFID antenna 215 includes a pot core half 700 and a toroidal wire coil 706 that fits within the pot core half. The two ends 710, 712 of the toroidal wire coil 706 are electrically coupled to the transceiver circuit 602 to transmit RF energy and detect modulated RF energy from the RFID tag 225 only when the pot core half 310 of the RFID tag is substantially aligned with and proximate to the pot core half 700 of the RFID antenna 215. The two ends 710, 712 of the toroidal wire coil 706 may be of sufficient length to allow the transceiver circuit 602 to be at some distance from the RFID antenna 215. The two ends 710, 712 of the toroidal wire coil 706 may extend through one or more gaps 708 in an outer pole of the pot core half 700.

The pot core half 310 of the RFID tag 225 and the pot core half 700 of the RFID antenna 215 will be configured with the open faces 300, 702 adjacent one another and separated by no more than a small distance, typically about 0.05 inch and generally less than 0.15 inch, such that a sterile barrier may be placed between them. The adjacent coils 302, 706 will be largely enclosed by the bases 306, 704 and outer poles 304, 714 of the two pot core halves 310, 700 which may shield the coils from nearby electrical interference. The substantial alignment of the poles of the two pot core halves 310, 700 may increase the electrical coupling of the adjacent coils 302, 706 and increase the signal strength while decreasing the noise coupling to improve the signal to noise ratio.

In some applications the surgical instrument 104, 106, 108, 110 may be installed in more than one orientation. For example, the endoscope 104 illustrated in FIG. 2 may be installed on the camera 102 in one of two orientations. The RFID reader 600 may contain one RFID antenna 215, 216 for each possible orientation of the surgical instrument 104. The RFID tag and antenna of the present invention provide sufficient selectivity that the RFID tag 225 will only be read by one antenna even if another antenna is nearby. For example, the two antennas may be less than two inches apart and still have only one of the two antennas respond to the RFID tag. Thus, the orientation of the surgical instrument 104 may be determined by which antenna 215, 216 receives modulated RF energy from the RFID tag 225. It will be appreciated that orientation of the surgical instrument 104 may also be determined by using a single RFID antenna and multiple RFID tags with each tag providing unique identification information.

Figure 8:
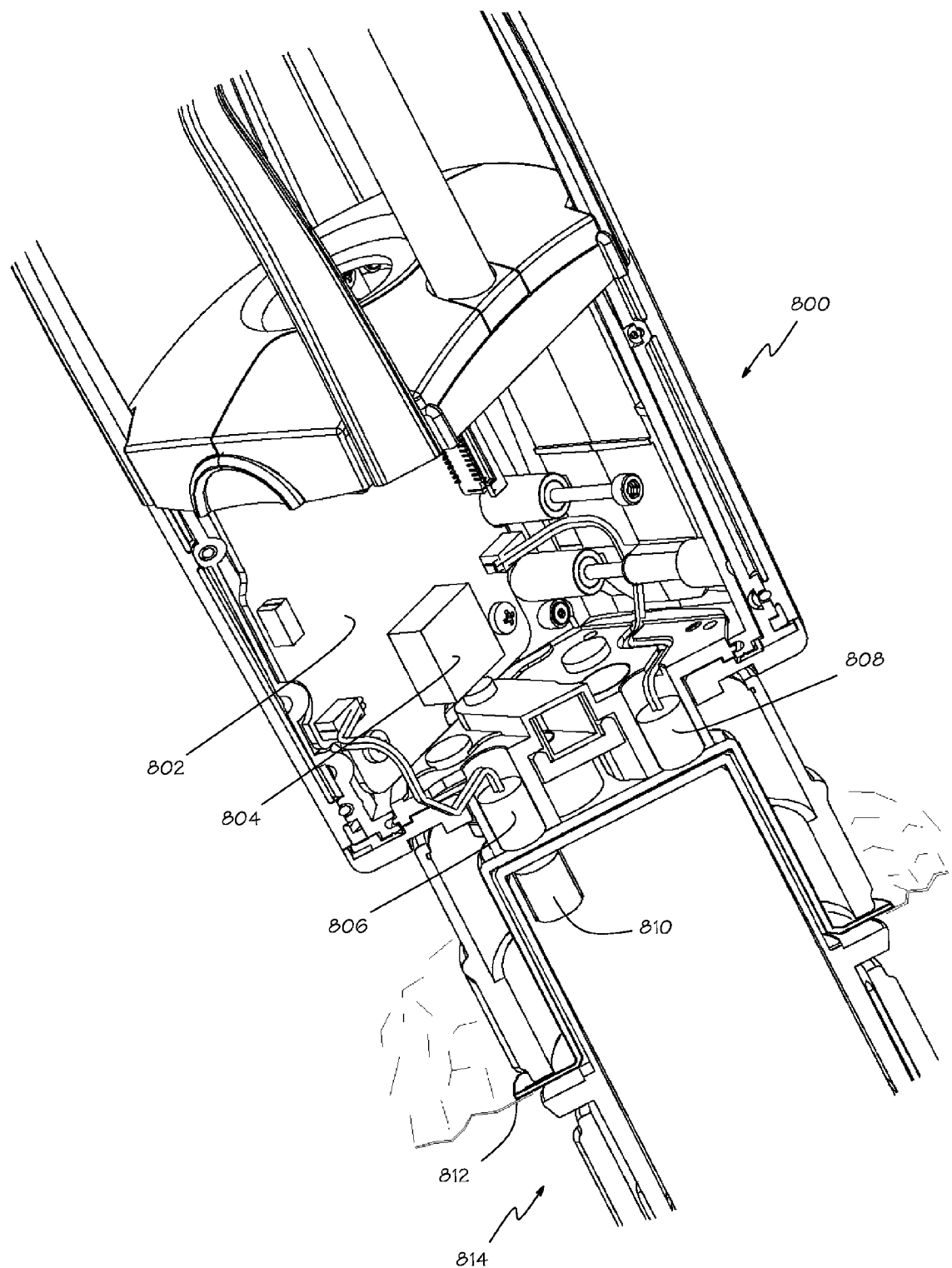
FIG. 8 is a cutaway view of a coupled endoscope and endoscopic camera that embodies the invention.

FIG. 8 is a cut-away view of another surgical robot 800 with coupled surgical instrument 814 that embodies the invention. The surgical robot 800 includes a RFID reader 802. The RFID reader includes an RFID transceiver circuit 804 coupled to two RFID antennas 806, 808. The surgical instrument 814 includes an RFID tag 810. The RFID antennas 806, 808 and the RFID tag 810 are constructed with a toroidal coil in a pot core half as previously described. The surgical instrument 814 is coupled to the surgical robot 800 with a sterile barrier 812 between them. The surgical instrument 814 is coupled to the surgical robot 800 such that the RFID tag 810 is substantially aligned with one RFID antenna 806 which will receive modulated RF energy from the RFID tag. The other RFID antenna 808 will not receive an appreciable amount of modulated RF energy from the RFID tag 810.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A radio frequency identification system comprising:
   a radio frequency identification reader that includes
   a radio frequency identification transceiver circuit,
   a first pot core half having a base, the base having a center pole and an outer pole extending from a first side of the base,
   a first toroidal wire coil that fits within the first pot core half around the center pole, the first wire coil terminated by two leads electrically coupled to the transceiver circuit to transmit and receive radio frequency energy,
   a second pot core half having a base, the base having a center pole and an outer pole extending from a first side of the base, wherein a distance between the first pot core half and the second pot core half is less than two inches, and
   a second toroidal wire coil that fits within the second pot core half around the center pole, the second wire coil terminated by two leads electrically coupled to the transceiver circuit to transmit and receive radio frequency energy; and
   a radio frequency identification tag that includes
   a radio frequency identification circuit assembly,
   a third pot core half having base, the base having a center pole and an outer pole extending from a first side of the base, and
   a third toroidal wire coil that fits within the third pot core half around the center pole, the third wire coil terminated by two leads electrically coupled to the radio frequency identification circuit assembly to modulate the radio frequency energy received from the first wire coil only when the third pot core half is substantially aligned with and proximate to the first pot core half and to modulate the radio frequency energy received from the second wire coil only when the third pot core half is substantially aligned with and proximate to the second pot core half.

2. The radio frequency identification system of claim 1, wherein the pot cores are constructed of a magnetic material with a high magnetic permeability.

3. The radio frequency identification system of claim 1, wherein the pot cores are constructed of ferrite.

4. The radio frequency identification system of claim 1, wherein the radio frequency identification circuit assembly transmits and receives radio frequency energy having a frequency of substantially 125 kHz.

5. A method of identifying a surgical instrument attached to a surgical robot, the method comprising:
   embedding a radio frequency identification tag on the surgical instrument, the radio frequency identification tag including
   a radio frequency identification circuit assembly,
   a first pot core half having a base, the base having a center pole and an outer pole extending from a first side of the base to a surface of the surgical instrument, and
   a first toroidal wire coil that fits within the first pot core half around the center pole, the first wire coil terminated by two leads electrically coupled to the radio frequency identification circuit assembly to modulate received radio frequency energy;
   providing a radio frequency identification reader on the surgical robot, the radio frequency identification reader including
   a radio frequency identification transceiver circuit,
   a second pot core half having a base, the base having a center pole and an outer pole extending from a first side of the base to a surface of the surgical robot that is adjacent the radio frequency identification tag when the surgical instrument is attached to the surgical robot, and
   a second toroidal wire coil that fits within the second pot core half around the center pole, the second wire coil terminated by two leads electrically coupled to the transceiver circuit to transmit radio frequency energy and receive modulated RF energy from the first wire coil only when the first pot core half is substantially aligned with and proximate to the second pot core half.

6. The method of claim 5, wherein the radio frequency identification reader further includes:
   a third pot core half having a base, the base having a center pole and an outer pole extending from a first side of the base to the surface of the surgical robot that is adjacent the radio frequency identification tag when the surgical instrument is attached to the surgical robot, and
   a third toroidal wire coil that fits within the third pot core half around the center pole, the third wire coil terminated by two leads electrically coupled to the transceiver circuit to transmit radio frequency energy and receive modulated RF energy from the first wire coil only when the first pot core half is substantially aligned with and proximate to the third pot core; and
   wherein the method further comprises identifying the orientation of the surgical instrument based on whether the second or third wire coil receives the modulated RF energy.

7. The method of claim 5, further comprising:
   embedding a second radio frequency identification tag on the surgical instrument, the second radio frequency identification tag including
   a second radio frequency identification circuit assembly,
   a third pot core half having a base, the base having a center pole and an outer pole extending from a first side of the base to a surface of the surgical instrument, and
   a third toroidal wire coil that fits within the third pot core half around the center pole, the third wire coil terminated by two leads electrically coupled to the second radio frequency identification circuit assembly to modulate received radio frequency energy;
   wherein the radio frequency identification circuit assembly coupled to the first wire coil provides a first identification code and the second radio frequency identification circuit assembly coupled to the third wire coil provides a second identification code.

8. The method of claim 5, further comprising providing a sterile barrier between the surface of the surgical instrument and the surface of the surgical robot.

9. The method of claim 5, further comprising transmitting and receiving radio frequency energy having a frequency of substantially 125 kHz with the radio frequency identification reader.

10. A radio frequency identification system comprising:
    a radio frequency identification reader that includes
    a radio frequency identification transceiver circuit,
    a first pot core half having a base, the base having a center pole and an outer pole extending from a first side of the base, and
    a first toroidal wire coil that fits within the first pot core half around the center pole, the first wire coil terminated by two leads electrically coupled to the transceiver circuit to transmit and receive radio frequency energy; and radio frequency identification tags that include
- a first radio frequency identification circuit assembly that provides a first identification code,
- a second pot core half having base, the base having a center pole and an outer pole extending from a first side of the base,
- a second toroidal wire coil that fits within the second pot core half around the center pole, the second wire coil terminated by two leads electrically coupled to the first radio frequency identification circuit assembly to modulate the radio frequency energy received from the first wire coil only when the second pot core half is substantially aligned with and proximate to the first pot core half,
- a second radio frequency identification circuit assembly that provides a second identification code,
- a third pot core half having a base, the base having a center pole and an outer pole extending from a first side of the base, wherein a distance between the second pot core half and the third pot core half is less than two inches, and
- a third toroidal wire coil that fits within the third pot core half around the center pole, the third wire coil terminated by two leads electrically coupled to the second radio frequency identification circuit assembly to modulate the radio frequency energy received from the first wire coil only when the third pot core half is substantially aligned with and proximate to the first pot core.

11. The radio frequency identification system of claim 10, wherein the pot cores are constructed of a magnetic material with a high magnetic permeability.

12. The radio frequency identification system of claim 10, wherein the pot cores are constructed of ferrite.

13. The radio frequency identification system of claim 10, wherein the radio frequency identification circuit assembly transmits and receives radio frequency energy having a frequency of substantially 125 kHz.

\* \* \* \* \*